United States Patent [19]
Hice

[11] Patent Number: 5,921,009
[45] Date of Patent: Jul. 13, 1999

[54] FOOT LEVERAGE SYSTEM AND METHOD

[75] Inventor: Gilbert A. Hice, Goldhill, Oreg.

[73] Assignee: Pivotal Image, Inc., Gold Hill, Oreg.

[21] Appl. No.: 08/879,658

[22] Filed: Jun. 20, 1997

[51] Int. Cl.⁶ .................................. A61F 5/14; A43B 7/24
[52] U.S. Cl. ................................. 36/140; 36/142; 36/143; 36/144; 36/43
[58] Field of Search ............................. 36/140, 142, 143, 36/144, 132, 43, 44, 71

[56] References Cited

U.S. PATENT DOCUMENTS

| | | | |
|---|---|---|---|
| 454,342 | 6/1891 | Gefvert | 36/161 |
| 1,287,810 | 12/1918 | Wojteck | 36/164 |
| 1,806,409 | 8/1931 | Nickerson | 36/145 |
| 1,958,097 | 5/1934 | Shaw | 36/144 |
| 2,616,190 | 11/1952 | Darby | 36/144 |

(List continued on next page.)

OTHER PUBLICATIONS

Christensen, J., Campbell, N., DiNucci, K., Closed Kinetic Chain Tarsal Mechanics of Subtalar Joint Arthroereisis; pp. 467, 472; Journal of the American Podiatric Medical Association; vol. 86, No. 10; Oct. 1996.

Tomaro, J., Burdett, R., Chadran, A., Subtalar Joint Motion and the Relationship to Lower Extremity Overuse Injuries; pp. 427, 432; Journal of the American Podiatric Medical Association; vol. 86, No. 9; Sep. 1996.

Roy, K., Scherer, P., Forefoot Supinatus; pp. 390–394; Journal of the American Podiatric Medical Association; vol. 76, No. 7; Jul. 1986.

Rossi, W., The Insole; pp. 306–307; Journal of the American Podiatric Medical Assoc.; vol. 70, No. 6; Jun. 1980.

Clinical Biomechanics, vol. II; Normal & Abnormal Functions of the Foot; pp. 129–132, 137, 139, 141, 143, 186–187, 205.

Dananberg, H., Lawton, M., DiNapoli, D., Hallux Limitus and Non–Specific Gait Related Bodily Trauma; pp. 52–58.

Janisse, D., Shoe Modifications, p. 103; Biomechanics; Feb. 1996.

Lee, T., Lin, S., Ruhl, Z., Treating Forefoot Pathology With Prefabricated Metatarsal Longitudinal Arch Support pp. 51–54; Biomechanics; Nov./Dec. 1996.

Clinical Biomechanics. vol. II; Normal and Abnormal Function of the Foot; pp. 73–77, 79–84, 122, 129–132, 135 149–150, 175–178, 371, 425 (1977).

Langer, S., To Control or Not to Control: That is the Question; pp. 57–59, 71; Biomechanics; Jun. 1996.

Wu, K., Foot Orthosis; Biomechanics of the Foot.

Wu, K., Foot Orthosis: Principles and Clinical Applications; pp. 39, 97–102, 104, 107 (1990).

Pressman, M., Biomechanics and Surgical Criteria for Flexible Pes Valgus; pp. 7–13; J. of American Podiatric Medical Assoc., vol. 77; No. 1; Jan. 1987.

Blake, R., Ferguson, H., Foot Orthosis for the Severe Flatfoot in Sports; pp. 549–555; J. of American Podiatric Medical Assoc., vol. 81; No. 10; Oct. 1991.

Kirby, K., The Medial Heel Skive Technique; pp. 177–188; J. of American Podiatric Medical Assoc., vol. 82; No. 4; Apr. 1992.

*Primary Examiner*—M. D. Patterson
*Attorney, Agent, or Firm*—James W. Pravel

[57] ABSTRACT

An adjustable dynamic, removable, mechanical foot leverage orthotic system is disclosed having a plate member positioned on top of a fulcrum member that are placed inside of a shoe. The plate is free to move within the shoe about the fulcrum to provide the wearer with mechanical improvement of abnormal, functional and associated foot pathology and can directly and indirectly effect the entire gait cycle. The foot leverage system can be integrated into the shoe design or can be inserted within a conventional shoe to create a foot leverage system. Methods of use and treatment are disclosed for the treatment of pes planus, pes cavus and tendonitis. The foot leverage system may also be used with the disclosed foot mapping system and method.

18 Claims, 6 Drawing Sheets

U.S. PATENT DOCUMENTS

| | | | |
|---|---|---|---|
| 3,292,612 | 12/1966 | Foss | 36/140 |
| 4,578,882 | 4/1986 | Talarico, II | 36/143 |
| 4,597,195 | 7/1986 | Dananberg | 36/28 |
| 4,608,988 | 9/1986 | Dananberg | 128/581 |
| 4,631,843 | 12/1986 | Annovi | 36/93 |
| 4,685,227 | 8/1987 | Simmons | 36/144 |
| 4,702,255 | 10/1987 | Schenkl | 36/145 |
| 4,744,157 | 5/1988 | Dubner | 36/88 |
| 4,759,357 | 7/1988 | Allart et al. | 36/44 |
| 4,777,739 | 10/1988 | Hiles | 36/43 |
| 4,800,657 | 1/1989 | Brown | 36/44 |
| 4,821,432 | 4/1989 | Reiber | 36/132 |
| 4,841,648 | 6/1989 | Shaffer et al. | 36/43 |
| 5,036,604 | 8/1991 | Rosen | 36/150 |
| 5,158,767 | 10/1992 | Cohen et al. | 36/88 |
| 5,184,409 | 2/1993 | Brown | 36/44 |
| 5,203,096 | 4/1993 | Rosen | 36/43 |
| 5,327,664 | 7/1994 | Rothbart | 36/174 |
| 5,345,701 | 9/1994 | Smith | 36/144 |
| 5,373,650 | 12/1994 | Dananberg et al. | 36/92 |
| 5,727,335 | 3/1998 | Kousaka et al. | 36/140 |

FOOT LEVERAGE SYSTEM AND METHOD

FIELD OF THE INVENTION

The present invention relates to the field of orthotic devices. More specifically, the present invention relates to a self-adjustable, or easily modified functional orthotic device and method of using the orthotic device.

BACKGROUND OF THE INVENTION

Orthotic inserts have been used for many years in an effort to correct the alignment and functional pathology of the human foot. U.S. Pat. No. 454,342 shows one of the earliest orthotic inserts used for the supportive, static, correction of a flat foot deformity. Such an insert is generally known as an "arch support."

More recent orthotic inserts allow for the variable placement of static components. For example, in U.S. Pat. No. 4,800,657, the insert provides adjustment plugs to "fine tune" the supportive contour of the insert. Another recent example is U.S. Pat. No. 4,841,648 which shows a supportive insole that can be modified by the user. The insole consists of different attachable insole pieces which vary in size, shape and density.

Although modern insert design, which is generally supportive in structure, can be indirectly effective in treating lower extremity functional pathology, they also can and often do fail to achieve a noticeable functional improvement. Ideally, a foot orthosis should be functional, supportive and comfortable. A foot orthosis should also be self-adjustable or easily modified to account for the variable lower extremity mechanical factors. The orthosis should treat the leg, ankle and foot as a system complex functioning through the total gait cycle. The foot orthosis should not be limited to the treatment of positional static biomechanical microcosms of the lower extremities. For example, static orthotic inserts, having a depression or a support, are commonly used to accommodate a callus. A callus however, should usually be treated dynamically because a callus is predominantly a functional foot problem. Unfortunately, the knowledge currently available does not include a direct treatment method to accomplish the results that the instant invention provides.

Sophisticated clinical examination techniques and, in some cases, computer monitored "pressure data" studies are used to establish a biomechanical basis and to confirm the effectiveness of the prescribed treatment using shoe inserts. Yet, in many instances, the supportive orthotic treatment prescribed does not correct the patient's foot disorder. It is not unusual for a foot specialist to make an illogical, if not questionable adjustment to an insert, based upon current treatment options and knowledge, and find that the adjustment corrected the symptomatic condition. This is because treatment knowledge has overlooked direct functional application of the orthosis, which is sometimes serendipitously achieved.

Because most patients can actually feel the normal neurological responses of the foot and lower extremities, they can often know when their body is more or less working properly as a result of their symptomatic conditions. Moreover, even when there is initial discomfort caused by an orthosis, the patient can often correctly predict future tolerance of the orthosis and improvement of the symptomatic condition. Although the foot specialist uses objective factors to correct foot disorders, he or she also uses subjective factors in evaluating the patients comfort with the prescribed orthosis. Therefore, the patient's subjective perspective can often be as important to correct treatment as the foot specialist's objective perspective.

Ideally, the objective of orthopedic foot treatment is to improve functional alignment and symptomology of the foot and lower extremities through as much of the gait cycle as possible. Generally speaking, even regarding mild foot pathology, an appropriate surgery is more likely to achieve the long-term goal of treatment in comparison with the use of a contemporary foot orthosis. The reason for the higher success rate of surgery is at least in part, because surgery can provide a more permanent functional alignment and symptomatic improvement. In addition, the combination of wear changing characteristics of a shoe and a conventional supportive orthotic insert which flattens with use, can be unpredictable. Another reason is because there is no conveniently effective positive adjustment mechanism for the inevitable deteriorating change of the shoe or insert.

Because of the expense, discomfort and potential risks associated with surgery, orthotic treatment devices are widely used to improve symptomatic conditions of the foot and lower extremities. Even with our most advanced analytical techniques however, we have only a basic idea of how each individual biomechanical system works as an efficient unit. This is especially true with respect to the foot and lower extremities. We know that we can alter the walking surface by using a shoe insert. The change in a walking surface creates a biomechanical system reaction extending from the foot proximally to the axial skeleton. In time, changing the position of the foot's anatomical alignment by supporting it with an insert can modify system function with the possibility of influencing the biomechanical activity through the total gait cycle. Nevertheless, current insert adjustments, even when effective, almost universally are considered by patients and doctors to be inconvenient, time consuming and costly. The result can be that the patient who needs to be treated will avoid seeing a foot specialist for as long as possible. This delay can cause the condition of the patient to deteriorate further.

What is needed is a shoe insert design and method of treatment that will allow the wearer to experience direct and immediate functional benefit and to make simple adjustments for improved function. Improved function should result in improved anatomical alignment. The patient should be able to take an active responsibility in the empirical treatment of themselves, with respect to varying circumstances. The device should allow a dynamic interaction between the wearer, the shoe and the insert to place the patient in more effective control of his or her treatment plan. Further, the orthosis should be adaptable to many types of conventional foot orthoses to enhance their capability to improve function and comfort to the wearer.

SUMMARY AND OBJECTS OF THE INVENTION

This invention relates to a new dynamic, removable, mechanical foot orthosis and shoe insole leverage system that is comprised of a plate overlaying a fulcrum upon which the plate functionally "see saws." The foot leverage system can be used together with conventional shoes by inserting the fulcrum and foot plate within the conventional shoe. The foot leverage system is a functional mechanism that can move the foot from one position to another without direct assistance from extrinsic or intrinsic muscle activity. Instead, it utilizes the naturally occurring displacement of the center of body pressure to create torque variations around the fulcrum which creates a resultant rotation of the plate and the foot about the fulcrum.

The rate of rotation of the inventive plate about the fulcrum can be changed by:

1. changing the rigidity of the plate;
2. adding or removing variable density materials or compressible spring-like materials on either side of the fulcrum;
3. modifying the modulus of elasticity of a hinge type fulcrum member that is positioned between the plate and the inner sole; or
4. modifying the dimensions, position and design of the inventive fulcrum.

The initiation of rotation in the stance phase as well as the direction or angle of movement of the foot-supporting plate, relative to the shoe, can be altered by changing the shape of the fulcrum in height, width, radius of curvature, length or position beneath the inventive plate.

In a preferred embodiment of the present invention, a uniform fulcrum is removably attached to the shoe sole or to the plate. The plate is positioned on the top of the fulcrum and typically extends to a position beyond the metatarsal heads. In another preferred embodiment, the fulcrum has an I-shaped cross section and has resilient, flexible material at the relatively narrow center section. In another preferred embodiment, the fulcrum varies in width, height and radius of curvature along its length. Another preferred embodiment includes resilient material, of desirable density, between the shoe sole and the inventive plate, in front and back of the inventive fulcrum. The resilient material is generally less dense than the density of the fulcrum material. The resilient material in front of the fulcrum is nearly always less dense than the density of the fulcrum to allow for the forward rotation of the plate and the wearer's foot. The density of the resilient material in front of the fulcrum can also be different than the density of the resilient material behind the fulcrum to allow for a different rate of rotation to the rear than to the front of the fulcrum.

In another preferred embodiment, the fulcrum is formed with a step-shaped ledge either on the inventive plate or integral with a shoe sole insert. Resilient material of desirable density, generally less than density of the fulcrum, may be positioned in the gap between the inventive plate and the top of the inner shoe sole or welt.

In another preferred embodiment, the inventive plate is molded to the identical or approximate shape of the user's foot.

The invention also describes a method for changing the force curve manifestation of the foot. The force curve, which is an indicator of function, can be changed by adjusting the inventive plate and fulcrum to arrest the abnormal force-related symptomatic conditions of the foot. An object of the present invention is to create a significant functional displacement of the force curve, either medially or laterally, from a pathologic path of progression to one that is more biomechanically and symptomatically desirable. As will be explained in more detail herein, this is achieved by creating torque variations around an artificial functional axis with the facility of simple positional reorientation. The positional reorientation is capable of directly or indirectly affecting the function of all of the periods of the gait cycle.

The invention also describes a method for treating different foot pathologies including: pes planus (excessively pronated low arched foot), pes cavus (excessively supinated high arched foot) and achilles tendonitis. By treating pes planus, the inventive method can prevent, reduce or eliminate many of the pathologic excessive pronatory sequelae such as: bunions, neuromas, hammertoes, hallux limitus, forefoot supinatus, plantar calluses, plantar fasciitis, cuboid syndrome, heel spur syndrome, tibialis posterior tendonitis, shin splints, medial knee retinaculitis and chondromalacia patella. By treating pes cavus, the inventive method can increase the stability of the lower extremities and improve the positional relationships of the foot structure to the leg. By treating achilles tendonitis, the inventive method can reduce stress and decrease or eliminate inflammation of the achilles tendon.

The invention also describes a mapping feature that directs the treating practitioner or the wearer to adjust the orthosis according to the symptomatic condition of the foot.

Another object of the present invention is to align more properly the foot and lower extremities which results from more efficient movement throughout the entire gait cycle. During the contact period, a plate in combination with a fulcrum of variable width and height supports the calcaneus posteriorly. During the midstance period, force displacement in the foot creates a shift of torque across the fulcrum which causes a rotation of the plate and produce appropriate associated motion and positional change in the foot and leg. During the propulsive period, the alignment and function of the foot and leg are improved relative to prior orthotic treatment systems and this alignment can carry into the swing phase.

Another object of the invention is to create a significant displacement of the force curve, either medially or laterally, from a pathological path of progression to one that is associated with less symptomology and that is more desirable. This is achieved with the present invention by creating torque variations about an artificial functional axis with the facility of simple positional reorientation of the fulcrum. The torque variations are capable of directly or indirectly affecting all periods of the gait cycle. An interplay of ground reactive force, plate reactive force and center of body pressure results in motion around the axis of the fulcrum. Sagittal, transverse and frontal plane motions of the inventive plate are directly influenced by fulcrum axis placement and shape which results in the simultaneous pronation or supination of the supported foot to variable degrees and within the variable time frame of the total gait cycle.

The present invention offers advantages over existing orthotic devices in that the instant orthotic device can:

1. directly generate mechanical foot function, primarily during midstance, which can be corrective and beneficial;
2. directly or indirectly affect the function of all periods of the gait cycle;
3. accommodate the wearer's needs as circumstances change by performing a simple adjustment;
4. be used to facilitate an existing shoe insert;
5. be worn by itself; and
6. be adjusted to fit with different shoe types that would otherwise not accept a standard type of insert.

The present invention changes the midstance function and position of the foot. The midstance period, during walking is the only complete time frame segment that a single foot supports the entire body weight. As such, midstance foot function has a significant impact upon the remainder of the gait cycle lower extremity function. By changing the midstance function and position of the foot, the rest of the gait cycle, including the swing cycle, can be indirectly effected.

Another advantage of the present inventive orthotic system is that the orthotic can be adjusted by the wearer to modify the shoe wear pattern. The resulting adjustment can reestablish foot balance in the worn shoe and redirect foot mechanics for more evenly worn shoes to enhance the shoe life and improve comfort.

Another advantage of the present inventive orthotic system is that the orthotic can be adjusted by the wearer to accommodate different physical or sport activities that are dependant upon efficient and specific lower extremity biomechanical function. For example, a golfer's swing may be improved by modifying the golfer's push-off shoe insert to provide better foot propulsion and an improved drive swing. The same individual may have a different propulsive requirement during a running activity and a simple adjustment to the fulcrum position can provide the desired change in function.

DETAILED DESCRIPTION

Figure 1A:
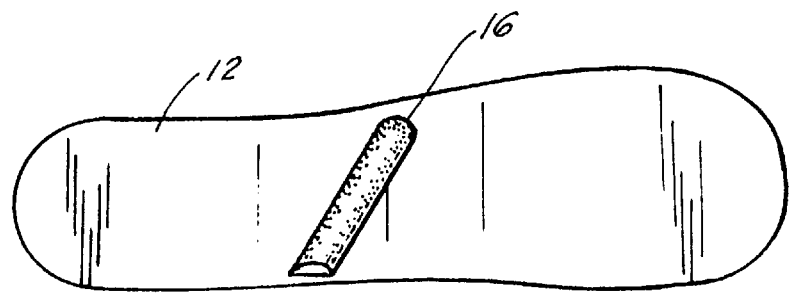
FIG. 1A is a top view of the inner side of the shoe sole with the fulcrum attached thereto.

The following table lists the part numbers and part descriptions as used herein and in the drawings attached hereto:

| Part No: | Description: |
| --- | --- |
| 12 | Inner Shoe Sole |
| 14 | Left Foot Plate |
| 15 | Right Foot Plate |
| 16 | Uniform Fulcrum |
| 18 | Flat Side of Fulcrum |
| 19 | Arcuate Side of Fulcrum |
| 20 | Flexible Hinge |
| 22 | Narrow Section of Flexible Hinge |
| 23 | Pin Fulcrum |
| 24 | First Variable Fulcrum |
| 25 | Fulcrum Seat |
| 26 | Second Variable Fulcrum |
| 28 | Forward Cushioning Material |
| 30 | Rearward Cushioning Material |
| 32 | Stepped Plate Fulcrum |
| 34 | Ledge |
| 35 | Inner Step |
| 36 | Lower Step |
| 38 | Stepped Sole Fulcrum |
| 40 | Pivot Ledge |
| 42 | Variable Pivot Ledge Modifier |
| 44 | Force Curve |
| 46 | Contoured Insole Plate for the Right Foot |
| 48 | Metatarsal Heads |
| 50 | Medial Side of Foot |

-continued

| Part No: | Description: |
| --- | --- |
| 52 | Lateral Side of Foot |
| 54 | Heel Lift |
| 58 | Right Plate - Front Region |
| 60 | Right Plate - High Arch Line |
| 62 | Right Plate - Low Arch Line |
| 64 | Right Plate - Achilles Tendonitis Line |
| 72 | Left Plate - Low Arch Region |
| 74 | Left Plate - Low Arch Line |
| 76 | Left Plate - Front Region |
| 78 | Left Plate - High Arch Line |
| 80 | Left Plate - High Arch Region |
| 82 | Achilles Tendonitis Region |
| 84 | Left Plate - Achilles Tendonitis Line |

Figure 1B:
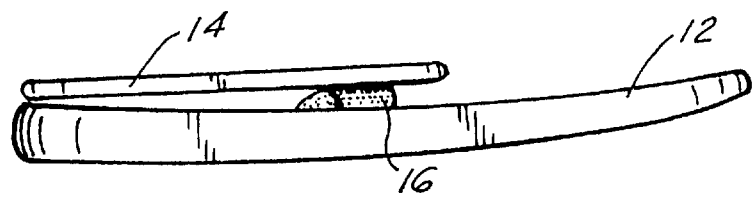
FIG. 1B is a side view of the inventive plate with the fulcrum attached to the top of the inner shoe sole and positioned between the plate and the top of the shoe sole.
Figure 1C:
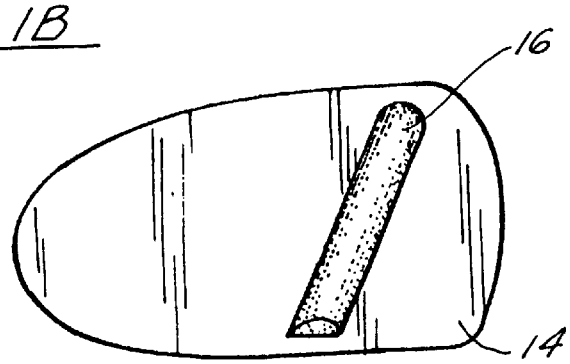
FIG. 1C is a bottom view (plantar-dorsal) of the inventive plate with the fulcrum attached thereto.
Figure 1D:
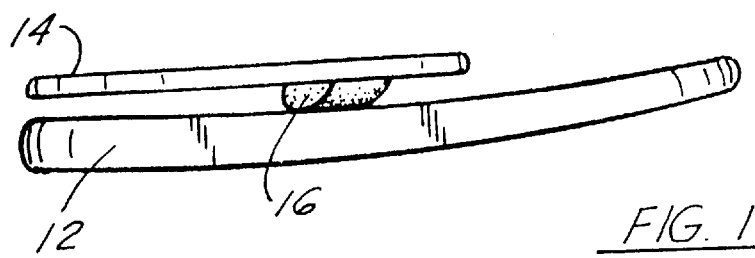
FIG. 1D is a side view of the inventive plate with the fulcrum attached to the plate and positioned between plate and the top of the shoe sole.
Figure 2A:
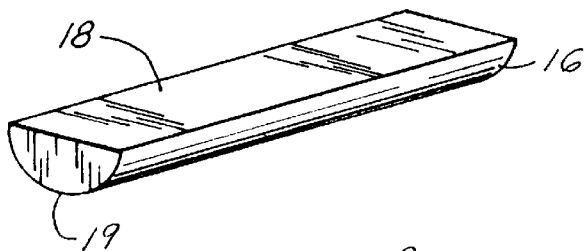
FIG. 2A is a perspective view of the uniform fulcrum.

In FIG. 1A the top of the inner shoe sole 12 is illustrated with the uniform fulcrum 16 attached thereto. The uniform fulcrum 16 has a flat side 18 and a curved side 19 as shown in FIG. 2A. Fulcrum 16 is attached to the top of the inner shoe sole 12 with a hook and loop faster material such as Velcro™ or other affixing means. FIG. 1B shows a side view of the left foot plate 14 positioned on top of the inner shoe sole 12 with the uniform fulcrum 16 sandwiched between the shoe sole 12 and the left foot plate 14. The uniform fulcrum 16 can be attached to the bottom of the inner shoe sole 12 as shown in FIGS. 1A and 1B or to the bottom of the left foot plate 14 as shown in FIGS. 1C and 1D.

The left foot plate 14 rotates forward and backward about the uniform fulcrum 16. The left foot plate 14 is typically made of a solid semi-rigid polypropylene material or a rigid graphite composite material. Although the left foot plate 14 is shown and described variously throughout this specification, the description applies equally to the right foot plate 15. The rigidity of the material is determined by the desired conditional response to the inventive foot leverage system. For example, if the wearer exhibits plantar fasciitis or is playing tennis, a less rigid foot plate 14, 15 may be appropriate whereas if the wearer exhibits cuboid syndrome or is running long distances, a more rigid foot plate 14, 15 may be appropriate.

Figure 2C:
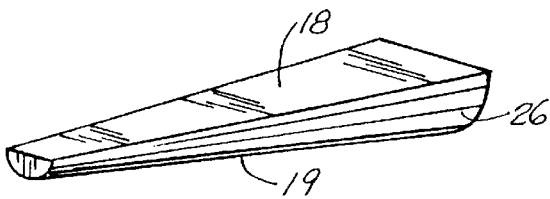
FIG. 2C is a perspective view of the second variable fulcrum.
Figure 2B:
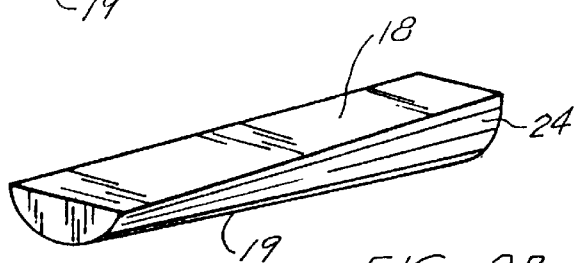
FIG. 2B is a perspective view of the first variable fulcrum.

The fulcrum may also be shaped with a tapered surface depending upon the desired functional characteristics between the foot plate 14, 15 and the fulcrum 16, 24, 26. FIG. 2B and FIG. 2C show two (2) possible variations in the taper of the fulcrum. Each of the fulcrums 16, 24, 26 includes a flat surface 18 for attaching a hook and loop fastener and a curved surface 19. As the foot plate 14, 16 moves forward and backward, it rotates about the curved surface 19.

Figure 1E:
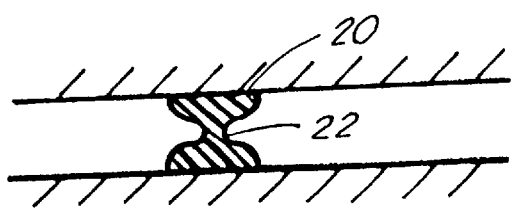
FIG. 1E is a sectional view of one embodiment of the present inventive fulcrum.

An alternative flexible hinge 20 may also be used in place of a fulcrum (see FIG. 1E). The flexible hinge 20 allows the inventive plate 14, 15 to rotate dynamically in a forward and rearward direction. The flexible hinge 20 is approximately I-shaped and has a flexible, narrow section 22 at the center of the I-shape. The flexible hinge is removably attached to the inner shoe sole 12 on one side and to the foot plate 14, 15 on the other. The flexible hinge 20 allows the foot plate 14, 15 to rotate forward and backward as the narrow section 22 flexes.

Figure 1F:
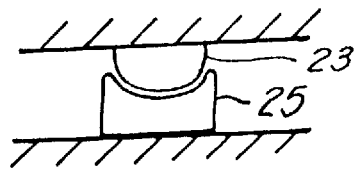
FIG. 1F is a sectional view of another embodiment of the present inventive fulcrum.

The fulcrum may also be constructed as a pin fulcrum 23 in combination with a fulcrum seat 25 as illustrated in FIG. 1F. The pin fulcrum 23 is removably attached at its upper face to the lower surface of the foot plate 14, 15. The fulcrum seat 25 is removably attached at its bottom surface to the inner shoe sole 12. The orientation of the pin fulcrum 23 and fulcrum seat 25 may also be reversed wherein the flat surface of the fulcrum seat 25 is removably attached to the bottom of the foot plate 14, 15 and the flat side of the pin fulcrum is attached to the inner shoe sole 12. The pin fulcrum 23 and fulcrum seat 25 combination allows the foot plate 14, 15 to rotate forward and backward as the convex surface of the pin fulcrum 23 rotates within the concave surface of the fulcrum seat 25.

Other variations in the configuration of the inventive fulcrum and plate are contemplated. For example, either the uniform fulcrum 16 or variable fulcrums 24, 26 may be used in combination with a fulcrum seat 25 as illustrated in FIG. 1F. The fulcrum seat 25 is normally attached to the inner sole of the shoe while the curved portion of the fulcrum 16, 24, 26 engages the upper, arcuate surface of the fulcrum seat.

Figure 3A:
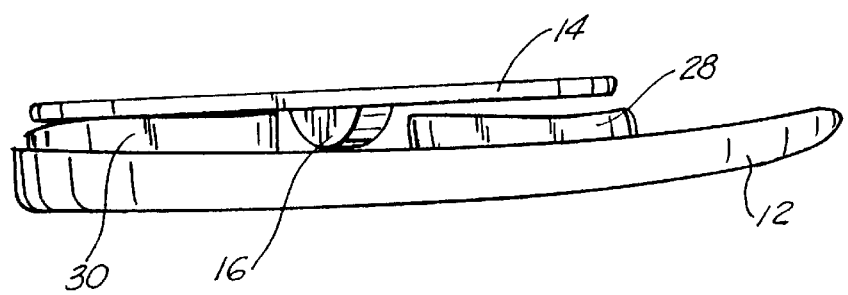
FIG. 3A is a side view of one embodiment of the inventive plate with one embodiment of the fulcrum and with variable density material between the plate and the shoe sole.
Figure 3B:
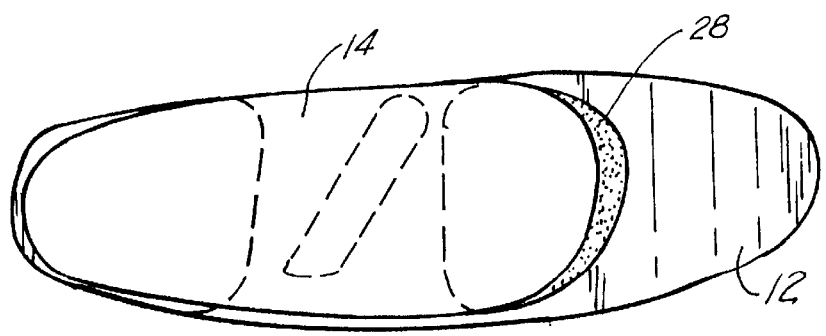
FIG. 3B is a top view of the embodiment shown in FIG. 3A.

FIG. 3A shows an embodiment similar to the embodiment shown in FIGS. 1A and 1B. In FIG. 3A a cushioning material 30 is positioned behind the uniform fulcrum 16, between the bottom of the left foot plate 14 and the top of the inner shoe sole 12. Cushioning material 28 is positioned in front of the uniform fulcrum 16, between the bottom of the left foot plate 14 and the top of the inner shoe sole 12. The density and resiliency of the cushioning materials 28, 30 can be varied according to the needs of the wearer. If desired, the properties of each cushioning material 28, 30 can be different. For example, it may be desirable to have less density in the rearmost cushioning material 30 and more density in the forward-most cushioning material 28 or visa-versa. Generally, the density of the forward-most cushioning material 28 is less than the density of the fulcrum thereby allowing for the forward rotation of the inventive plate and foot.

Figure 4A:
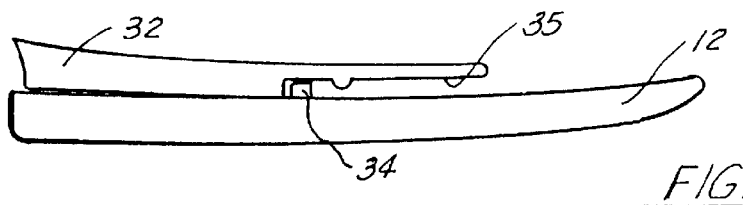
FIG. 4A is a side view of an embodiment of the present invention having a step-like fulcrum plate.
Figure 4B:
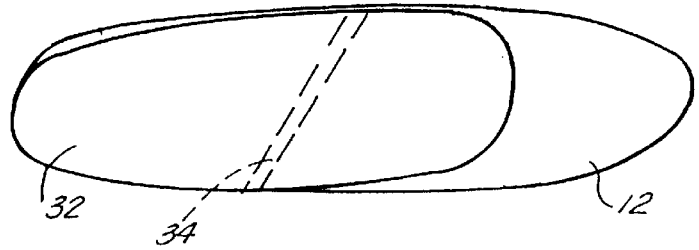
FIG. 4B is a top view of an embodiment of the present invention having a step-like fulcrum plate.
Figure 4C:
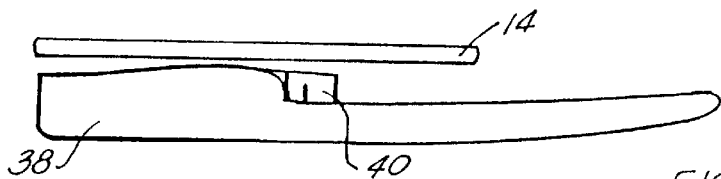
FIG. 4C is a side view of an embodiment of the present invention having a step-like fulcrum shoe sole.
Figure 4D:
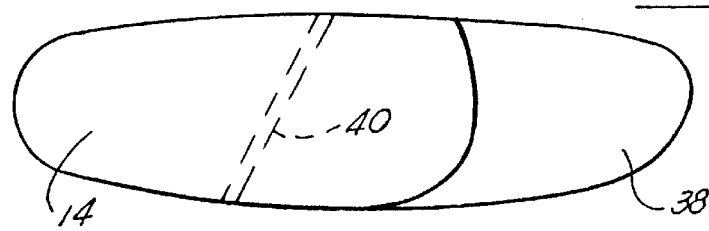
FIG. 4D is a top view of an embodiment of the present invention having a step-like fulcrum shoe sole.
Figure 4E:
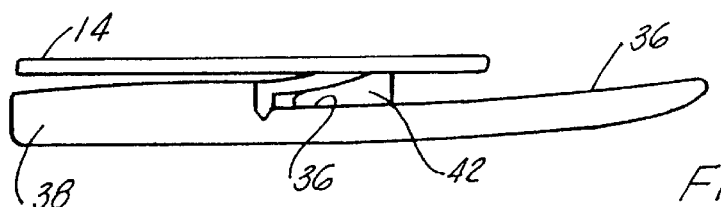
FIG. 4E is a side view of an embodiment of the present invention having a step-like fulcrum shoe sole and a fulcrum modifier of adjustable, variable density material beneath the plate.
Figure 4F:
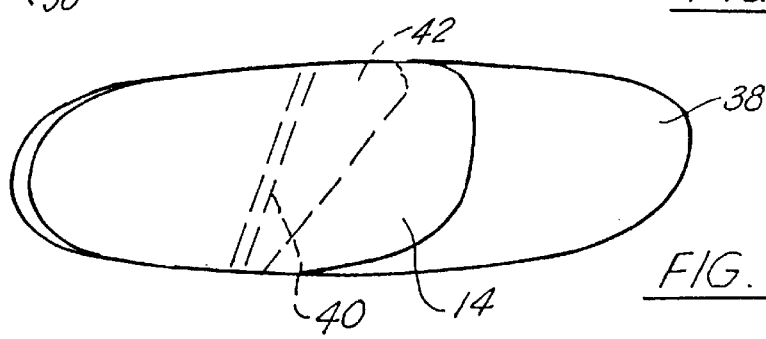
FIG. 4F is a top view of an embodiment of the present invention having a step-like fulcrum shoe sole and a fulcrum modifier of adjustable, variable density material beneath the plate.

Another preferred embodiment is shown in FIGS. 4A, 4B, 4C, 4D, 4E and 4F. In FIG. 4A a stepped plate fulcrum 32 is positioned on top of the inner shoe sole 12. The stepped plate fulcrum 32 is free to rotate forward about the ledge 34 and rearward to the position illustrated. The angle of the ledge 34 can be changed according to the desired functional reaction between the stepped plate fulcrum 32 and the inner shoe sole 12. FIG. 4C shows a modification of the ledge fulcrum feature wherein the fulcrum is created by forming a ledge 40 on a stepped shoe sole 38. The left foot plate 14 is free to rotate forward about the ledge 40 and rearward to the position illustrated. The angle of the ledge 40 can also be changed according to the desired functional reaction between the stepped shoe sole 38 and the inner shoe sole 12. A variable pivot ledge modifier 42 that is constructed of material of a desired density can be positioned in front of either ledge 34 or 40, between the stepped plate 35 and the sole 12 or between the left foot plate 14 and the stepped sole 38, respectively. FIG. 4F shows the variable pivot ledge modifier 42 positioned in front of the ledge 40, between the left foot plate 14 and the lower step portion of the stepped shoe sole 38. The variable pivot ledge modifier could also be placed in front of the step 34, below the inner step 35 and on top of the shoe sole 12. The density and resiliency of the variable pivot ledge modifier 42 can be changed to create the desired functional relationship between the stepped plate fulcrum 32 and the shoe sole 12 or between the stepped sole fulcrum 38 and the left foot plate 14.

Figure 5A:
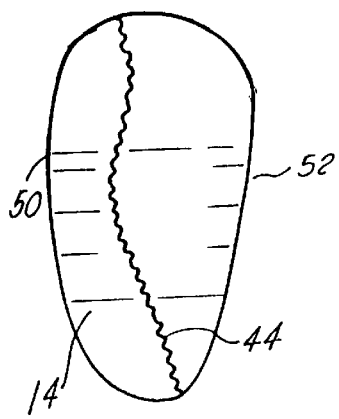
FIG. 5A is a plantar-dorsal view of a left foot plate showing a force curve of a supported foot when the foot is excessively pronated without the inventive fulcrum.
Figure 5B:
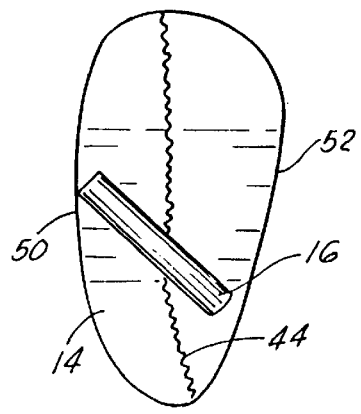
FIG. 5B is a plantar-dorsal view of a left foot plate showing an improved force curve of the foot when the plantar-attached inventive fulcrum and plate are being used.
Figure 5C:
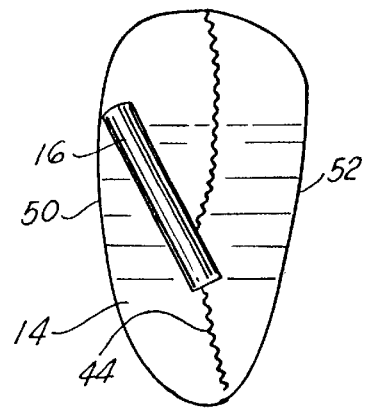
FIG. 5C is a plantar-dorsal view of a left foot plate showing the best, improved force curve of the foot when the inventive fulcrum and plate are being used and when the position of the plantar-attached fulcrum has been adjusted.

In FIGS. 5A, 5B and 5C the plantar-dorsal view (from the bottom looking up) of the left foot plate 14 is shown. The force curve of a foot 44 is shown along the medial line of the inventive plate. The force curve 44 represents the path in which body weight is transmitted through the foot during the stance phase of the walking gait cycle on the left foot plate 14. As previously indicated, an important objective of the present invention is to create a significant displacement of the force curve 44, either medially or laterally, from a pathological path of progression to one that is more desirable. This is achieved by creating torque variations around the artificial functional axis created by the left foot plate 14 or right foot plate 15 and fulcrum 16 system. The axis of rotation about the fulcrum 16 is applied externally to the plantar aspect of the plate 14, 15 relative to the foot. An interplay of ground reactive force, plate reactive force and center of body pressure results in motion about the axis. Sagittal, transverse and frontal plane motions are influenced by axis placement and shape resulting in a simultaneous pronation or supination to variable degrees within the variable time frame of the total gait cycle. In FIG. 5B, the improvement in the alignment of the force curve 44 from the medial side 50 toward the lateral side 52 of the foot is shown as a result of incorporating the uniform fulcrum 16 (shown in its relative position) beneath the foot plate 14, 15. If the position of the uniform fulcrum 16 is adjusted for the specific functional pathology of the wearer's foot, the force curve 44 can be further improved as illustrated in FIG. 5C.

Figure 6A:
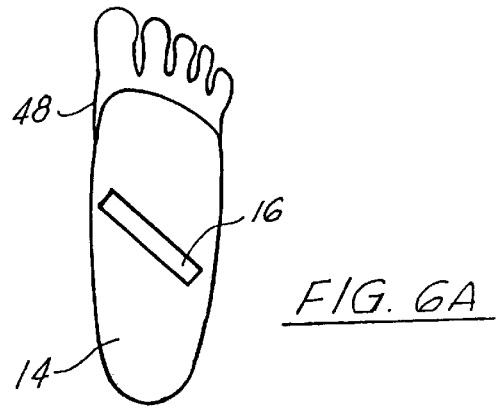
FIG. 6A is a bottom view (plantar-dorsal) of the left foot position relative to one embodiment of the inventive plate and fulcrum.
Figures 6B, 6C:
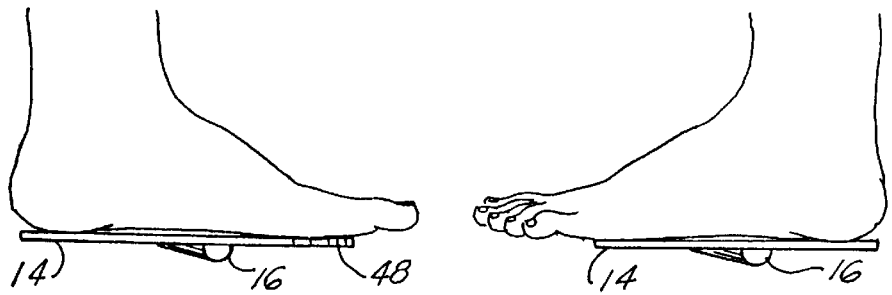
FIG. 6B is a right side view of the left foot position relative to one embodiment of the inventive plate and fulcrum.
FIG. 6C is a left side view of the left foot position relative to one embodiment of the inventive plate and fulcrum.

FIGS. 6A, 6B and 6C illustrate the desired position of the left flat plate 14 position relative to a left foot. The distal end of the left foot plate 14 extends to the area of the metatarsal heads 48. This allows the foot leverage system to support properly the entire weight of the body while allowing the wearer to exert pressure directly on the shoe insole with his or her digits during the propulsion stage of the gait cycle.

Figure 6D:
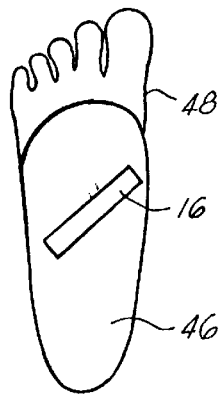
FIG. 6D is a bottom view (plantar-dorsal) of the right foot position relative to a contoured embodiment of the present inventive plate and fulcrum.
Figure 6E:
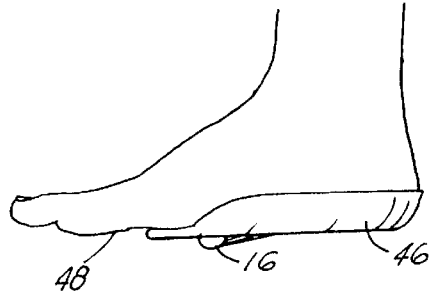
FIG. 6E is a side view of the right foot position relative to a contoured embodiment of the present inventive plate and fulcrum.

The invention may also use a conventional contoured plate 46 as shown in FIGS. 6D and 6E. The contoured plate 46 may be molded to a generic shape to approximate the size of the wearer's foot or may be custom molded for maximum comfort. The distal end of the contoured plate 46 may extend to a point proximal to the metatarsal heads 48, but may also extend to a position beyond the toes with a flexible insert extension.

Figure 7A:
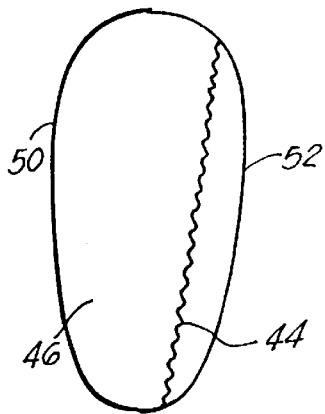
FIG. 7A is a top view (dorso-plantar) of a contoured plate showing a force curve when a right foot on the plate is excessively supinated without the inventive fulcrum.
Figure 7B:
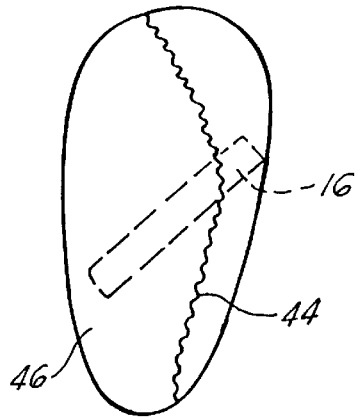
FIG. 7B is a dorso-plantar view of a contoured plate showing an improved force curve of the right foot with the plantar-attached inventive fulcrum in position.

In FIG. 7A and 7B the result of using the present inventive foot leverage system on the force curve 44 is illustrated and is representative of a person who has a high arch. A person who has a high arch has a propensity to experience inversion ankle sprains for which this invention is intended to prevent, reduce, or correct. In FIG. 7A, the center of force curve 44 of a supinated right foot on the contoured plate 46 is shown. In FIG. 7B, the effect of the use of the contoured plate 46 with the plantar inventive uniform fulcrum 16 is shown. It should be understood that when desirable, either of the variable fulcrums 24, 26 may be substituted for the uniform fulcrum 16. The interaction between the contoured plate 46 and the uniform fulcrum 16 creates a desirable net pronatory torque around the uniform fulcrum 16 during the midstance period. The resulting force curve 44 illustrates the change in the pressure caused by the wearer's body weight upon the contoured plate 46. The change in pressure illustrated in the force curve 44 helps to reduce the tendency for late midstance and propulsive period inversion ankle sprains, lateral shoe wear and fifth metatarsal head callus by leveraging the weight medially.

Figure 8A:
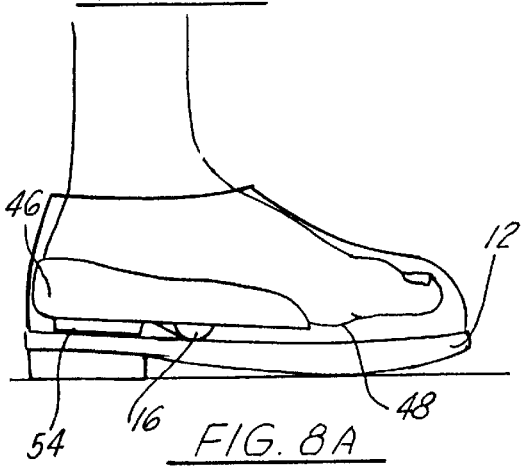
FIG. 8A is a side view of a foot in a contoured embodiment of the inventive plate and fulcrum with the heel and ball of the foot in the rearward position.
Figure 8B:
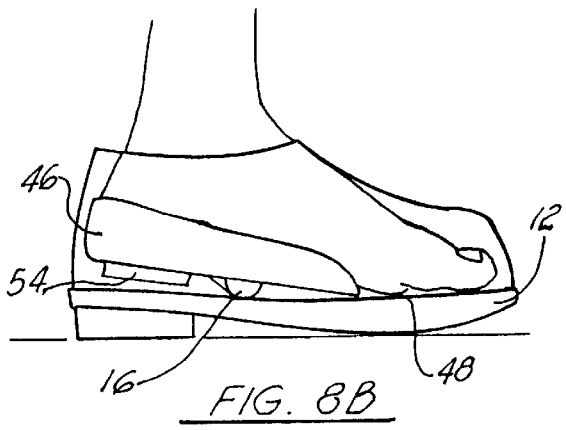
FIG. 8B is a side view of a foot in a contoured embodiment of the inventive plate and fulcrum with the calcaneus and midtarsal joints of the foot in the forward rotated position.

FIGS. 8A and 8B present a side view of the left foot with a cutaway view of the shoe to show clearly the position of the foot relative to the contoured plate 46 as it rotates about the uniform fulcrum 16 relative to the inner sole 12 of the shoe. As the wearer enters the late midstance period, or the early propulsive period of the gait cycle (depending upon fulcrum used and fulcrum placement), the foot rotates forward about the fulcrum as shown in FIG. 8B. The metatarsal heads 48 and the digits fully contact the top of the inner sole 12 of the shoe. The contoured plate may also include a heel plate 54 on the bottom of the contoured plate 46 to engage uniformly the top of the inner sole 12 above the calcaneus region for a prescribed heel contactMethod of ientation of the plate 46.

Method of Specific Treatment

The present inventive foot leverage system is effective to treat excessively pronated low arched foot types (pes planus). In FIG. 5A the force curve 44 reflects the pressure on the left foot before treatment relative to a left foot plate 14. The force curve 44 indicates excessive pronation of the foot. The fulcrum 16 is oriented in a position substantially aligned with the subtalar axis as shown in FIG. 5B. Also illustrated in FIG. 5B is the partially corrected force curve 44 that is aligned closer to the central portion of the plate as compared with FIG. 5A. FIG. 5C shows a more desirable force curve 44 that is generated when the position of the fulcrum 16 is adjusted according to the specific functional pathology of the wearer. The resulting supination is mechanically produced by the inventive foot leverage system during the midstance or during the propulsive period (depending upon fulcrum used and fulcrum placement); or both. The resulting supination is a triplanar motion that is described by an axis of rotation oriented posterior, plantar and lateral to anterior, dorsal and medial. The motion of supination is the opposite of pronation. The weight bearing, closed kinetic chain, subtalar joint supination produces calcaneal inversion with talar abduction and talar dorsiflection. The resulting desirable and directed foot supinatory motions occur simultaneously and facilitate more normal lower extremity function during the midstance and propulsive periods of the gait cycle. Pathological conditions associated with midstance and propulsive pronatory motion may be lessened or eliminated with the present invention and method of use, include: bunions, neuromas, hammertoes, hallux limitus, forefoot supinatus, plantar calluses, plantar fasciitis, cuboid syndrome, heel spur syndrome, tibialis posterior tendonitis, shin splints, medial knee retinaculitis and chondromalacia patella.

The present inventive foot leverage system is also effective in treating excessively supinated high arched foot types (pes cavus). In FIG. 7A, the force curve 44 is shown of a wearer who is afflicted with pes cavus. The force curve 44 is positioned excessively toward the lateral side 52 of the right foot plate. The present invention and method of use can restrict excessive subtalar joint supination through the generation of a pronatory torque across the subtalar joint axis using the proper placement of the fulcrum 16 as shown in FIG. 7B. After the wearer applies weight to the inventive foot leverage system, the resulting force curve 44 shown in FIG. 7B is produced. The resulting force curve 44 is generated by leverage to approximate a more normal orientation of the foot and lower extremity weight bearing forces. Pathological conditions associated with excessive midstance supination that may be lessened or eliminated with the present invention and method of use include: a sprained ankle, cuboid syndrome, peroneal tendonitis and lateral foot column calluses.

The present inventive foot leverage system is also effective to treat achilles tendonitis. The achilles musculotendinous complex passes the knee, ankle and subtalar joints. Normally, during the midstance period the ankle is dorsiflexing and generating a mild amount of internal leg rotation which contributes adversely to an abnormally pronated subtalar joint and its associated pathology. As dorsiflexion progresses, eccentric contraction of the gastrocnemius muscle provides knee flexion tension and the soleus decelerates the tibia which helps to extend the knee in smooth preparation for the propulsion stage of the gait cycle. The present inventive foot leverage system generates a reduced net amount of ankle joint dorsiflexion during the midstance period around the fulcrum which facilitates a more uniformly stressed and less physiologically strained achilles tendon. The leverage system can be adjusted to reduce the tendon strain without interfering significantly with the knee extension mechanism. The fulcrum can also be oriented or shaped to facilitate subtalar joint supination to improve the alignment effect on tendon fiber torque. The fulcrum can also be adjusted to initiate ankle acceleration into plantarflexion which creates an inertial reduction in the force required by the achilles tendon to flex the knee and lift the heel as the propulsive period is established. The rate of plantarflexion acceleration can be adjusted by:

1. altering the position of the fulcrum from a position proximate to the calcaneus to a position toward the midtarsal joints,
2. adding or modifying the durometer of resilient, spring-like material, anterior to the fulcrum, or
3. changing the rigidity of the plate.

Stress on the achilles tendon can be reduced by adding a heel lift heel plate 54 as shown in FIGS. 8A and 8B. The heel lift 54, lifts the heel off the inner sole 12 of the shoe. In combination with the foot leverage system, the heel lift 54 reduces the torque that is typically associated with the use of a static heel lift device alone. Conventional static heel lift devices simply maintain the heel in a static weight bearing position and can generate contractured, shortened states. Alternative conventional treatment involves stabilizing the tendon by casting or by realigning the tendon with an orthotic device. In contrast to a static heel lift, the instant invention allows the foot to enter the midstance period approximately perpendicular to the leg which allows a prescribed beneficial physiological stretch to the leg muscle during the contact and early midstance periods. As the foot dorsiflexes through midstance and the leg muscle is further stretched, the contoured insole plate 46 plantarflexes over the fulcrum 16 and rotation occurs lifting the heel and effectively reduces the force acting on the achilles tendon (see FIG. 8B). Foot and plate rotational modification can be achieved by adjusting height to the heel lift 54, by moving the fulcrum 16 forward or backward, beneath the contoured insole plate 46, by providing a thicker or thinner fulcrum 16, by lengthening or shortening the plate, or by forming a contoured insole plate 46 having an upward foot-contouring curvature relative to the plate-contact dimensions of the foot.

Figure 9C:
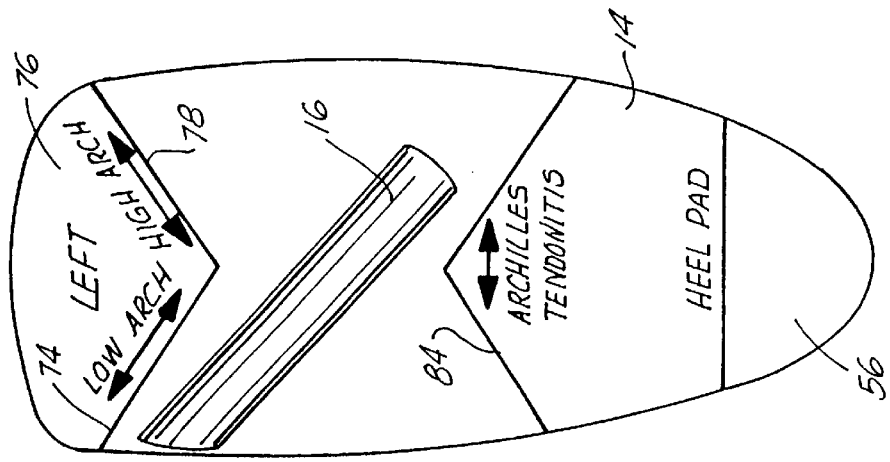
FIG. 9C is a bottom view of a the inventive plate for the left foot showing a fastening surface for fulcrum placement and a fulcrum in the appropriate position to treat a low arch foot.
Figure 9B:
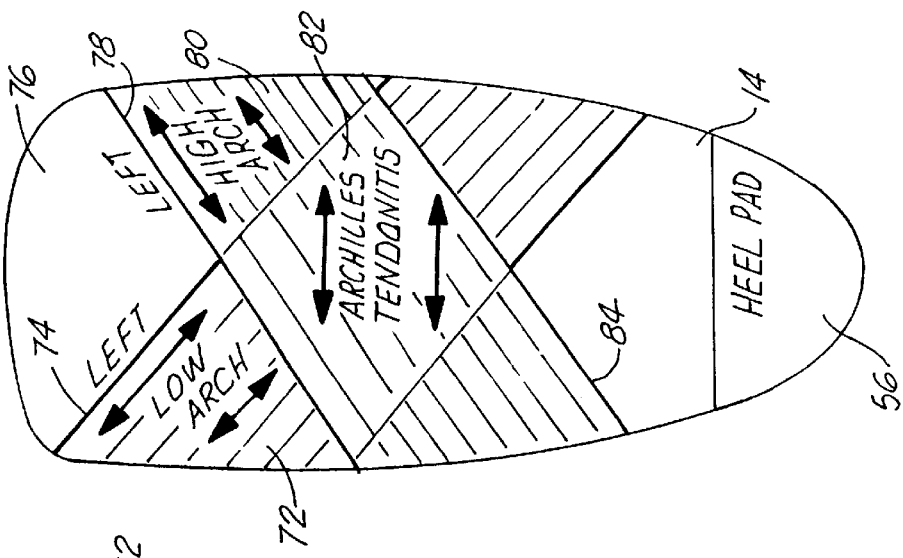
FIG. 9B is the reference positional map showing an illustration of the bottom view of the left foot plate and directing fulcrum placement on the inventive plate relative to specific symptomatic conditions.
Figure 9A:
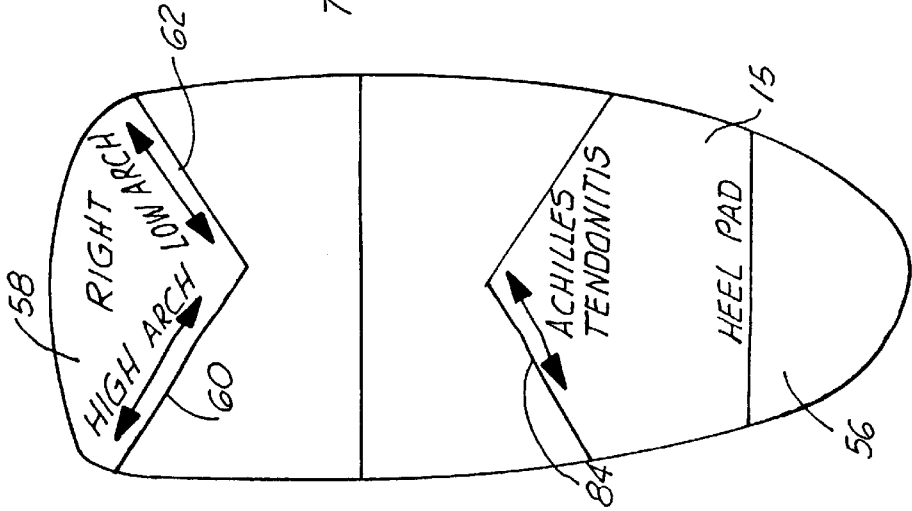
FIG. 9A is a bottom view of a plate for the right foot and a fastening surface for fulcrum placement without an attached fulcrum.

FIGS. 9A, 9B and 9C illustrate a new mapping method that is described herein relative to the embodiment illustrated in FIG. 1B, which can be used to facilitate proper and efficient application of the instant inventive foot leverage system. FIG. 9A illustrates the underside of the right foot plate 15 without a fulcrum 16 and FIG. 9C illustrates the underside of the corresponding left foot plate 14 with a fulcrum 16. FIG. 9B illustrates a directive map for placement of the fulcrum on the underside of the left foot plate illustrated in FIG. 9C. In FIG. 9A, the area between lines 60, 62 and 64 is generally covered with a fastener material such as hook and loop fasteners. In FIG. 9B and 9C, the fastener material is indicated on the map (FIG. 9C) between lines 74, 78 and 84. The corresponding side of hook and loop fastener is attached to the flat side 18 of the fulcrum 16. In FIG. 9B the high arch line 78, and the low arch line 74 are used as guide lines for properly adjusting the position of the top end of the fulcrum 16 to the plate shown in FIG. 9C. In FIG. 9B, the achilles tendonitis line 82 is used as a reference guide for properly adjusting the position of the fulcrum 16 on the left foot plate 14 shown in FIG. 9C. For example, to treat a patient who exhibits symptomatic conditions of a flattening arch, with respect to the left foot, the fulcrum 16 would be placed on the left foot plate 14 shown in FIG. 9C generally parallel to the line 74 as directed by the map shown in FIG. 9B and confirmed by line 74 on the plate shown in FIG. 9C. In FIGS. 9B and 9C, the position of the left low arch line 74 and high arch line 78 are reversed relative to the orientation of the corresponding lines 62, 60 on the right plate shown in FIG. 9A. The most specific beneficial adjustment of the fulcrum on the left foot plate 14 would be accomplished on the left foot plate 14 according the to the symptomatic response of the patient's foot to the position of the fulcrum.

The mapping method directs both professionals and laymen alike, to adjust the fulcrum 16 to achieve the most beneficial symptomatic orientation of the fulcrum on the plate 14, 15. The mapping method may similarly be used with fulcrums 23, 24, 26 in combination with the desired foot plate 14, 15, 46. Because of individual biodynamic uniqueness, further refined adjustment to the fulcrum position, based upon personal comfort and effect, may assist to further reduce symptomatic conditions and to establish the desired patient comfort.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed is:

1. A foot leverage system intended to be used with a shoe having a sole member, wherein the sole member has an inner side upon which the system functions, comprising:
    a. a semi-rigid plate member having a top side and a bottom side; said plate member sized in relative proportion to a shoe;
    b. a fulcrum having an upper face, a lower face, a first end and a second end;
    c. said fulcrum being positioned substantially aligned in a horizontal plane in the range of approximately nine degrees to eighty-five degrees from a longitudinal axis of the foot under the bottom side of said plate member and above the inner side of the sole member;
    wherein said first end of said plate extends unrestricted beyond the position of said fulcrum whereby said plate is free to rotate fore and aft about said fulcrum within the shoe relative to the sole member.

2. A foot leverage system used with a shoe having an sole member as claimed in claim 1, wherein said fulcrum has an arcuate upper surface and a substantially flat lower surface.

3. A foot leverage system used with a shoe having an sole member as claimed in claim 1, wherein said fulcrum has a substantially flat upper surface and an arcuate lower surface.

4. A foot leverage system as claimed in claim 1 in combination with a shoe having an sole member, wherein said foot leverage system also has a seat member having a concave upper surface and a substantially flat lower surface; said fulcrum having a convex lower face and a substantially flat upper face; said seat member being removably attached about said lower surface to the inner side of said sole member; said fulcrum being removably attached about said upper face to the bottom side of said plate; said arcuate lower face of said fulcrum being sized and shaped to rotatably engage the concave uppers surface of said seat member; whereby said fulcrum and said plate can rotate about said fulcrum seat.

5. A foot leverage system used with a shoe having a sole member as claimed in claim 2, wherein said fulcrum is adjustably secured to the sole member.

6. A foot leverage system used with a shoe having a sole member as claimed in claim 3, wherein said fulcrum is adjustably secured to said plate member with an attachment member.

7. A foot leverage system as claimed in claim 1, wherein said fulcrum has a substantially flat upper surface and a substantially flat lower surface; said fulcrum further having a variable cross section across the thickness of the fulcrum wherein the width of the cross section tapers at a point between the upper surface and the lower surface; whereby said upper and said lower surface can move relative to one another.

8. A foot leverage system as claimed in claim 1, wherein a material of a selectable density is positioned beneath the bottom side of said plate member.

9. A foot leverage system as claimed in claim 1, wherein said fulcrum tapers from the first end toward the second end.

10. A foot leverage system as claimed in claim 1, wherein said plate member is substantially contoured in relative proportion to a foot.

11. A foot leverage system as claimed in claim 1, wherein said fulcrum is integral to said plate member and whereby the thickness of said fulcrum is substantially uniform in thickness about the calcaneus region of said plate.

12. A foot leverage system as claimed in claim 1, in combination with a shoe having a sole member wherein said fulcrum is integral to the inside of the sole member and whereby the thickness of said fulcrum is substantially uniform in thickness about the calcaneus region of the sole member.

13. A foot leverage system as claimed in claim 1, wherein said plate member is substantially rigid in construction.

14. A foot leverage system as claimed in claim 1 wherein said fulcrum is positioned oblique to the longitudinal axis of said plate.

15. A foot leverage system as claimed in claim 1 wherein a predetermined modifier comprised of a compressible material is positioned under the bottom side of said plate member whereby the rate of rotation of said plate about said fulcrum is modified.

16. A dynamic, removable, mechanical foot leverage system intended to be used with a shoe having an sole member, wherein said sole member has an inner side, comprising a plate means having a top side and a bottom side for supporting the weight of the foot from the heel to the forefoot; said plate means being sized in relative proportion to a shoe; a fulcrum means having an upper face, a lower face, a first end and a second end, positioned substantially oblique to the longitudinal axis of said plate means, between the sole member and said plate means for providing a pivoting axis about which said plate means is free to move fore and aft within the shoe.

17. A method of providing an improved orthotic system for use by and treatment of a user's foot, wherein the orthotic system has a sole member having an inner side, comprising the steps of:

a. providing a plate member having a top side and a bottom side; said plate member sized in relative proportion to a shoe sole from the heel to the forefoot;

b. providing a fulcrum having an upper face, a lower face, a first end and a second end;

c. positioning an adjustable fulcrum under the bottom side of said plate member, substantially aligned in a horizontal plane in the range of approximately nine degrees to eighty-five degrees from a longitudinal foot axis and above the inner side of the sole member, said plate extending unrestricted beyond said fulcrum whereby said plate is free to move about said fulcrum within the shoe relative to the inner sole member.

18. A foot leverage system as claimed in claim 17, wherein a predetermined modifier comprised of a compressible material, is positioned under the bottom side of said plate member whereby the rate of rotation of said plate about said fulcrum is modified.

* * * * *